United States Patent
Schneid

(10) Patent No.: US 8,713,996 B2
(45) Date of Patent: May 6, 2014

(54) METHOD FOR DETERMINING THE FILTERABILITY OF BEER

(75) Inventor: Ralph Schneid, Freising (DE)

(73) Assignee: Krones AG, Neutraubling (DE)

( * ) Notice: Subject to any disclaimer, the term of this patent is extended or adjusted under 35 U.S.C. 154(b) by 252 days.

(21) Appl. No.: 13/132,751

(22) PCT Filed: Nov. 24, 2009

(86) PCT No.: PCT/EP2009/008364
§ 371 (c)(1),
(2), (4) Date: Aug. 5, 2011

(87) PCT Pub. No.: WO2010/063392
PCT Pub. Date: Jun. 10, 2010

(65) Prior Publication Data
US 2012/0090413 A1    Apr. 19, 2012

(30) Foreign Application Priority Data

Dec. 4, 2008   (DE) .................... 10 2008 060 446

(51) Int. Cl.
*B01D 61/58*   (2006.01)
*G01N 15/02*   (2006.01)

(52) U.S. Cl.
USPC ........ 73/61.63; 73/61.62; 73/61.68; 73/61.71

(58) Field of Classification Search
USPC ............. 73/61.62, 61.63, 61.65, 61.68, 61.73
See application file for complete search history.

(56) References Cited

U.S. PATENT DOCUMENTS

| | | | | |
|---|---|---|---|---|
| 2,572,436 A | * | 10/1951 | Boucher et al. | ............. 73/61.63 |
| 3,945,243 A |  | 3/1976 | Ouvrard | |
| 4,073,954 A | * | 2/1978 | Mobius | ....................... 426/330.3 |
| 4,257,259 A | * | 3/1981 | Ford | ............................. 73/61.56 |
| 4,563,441 A | * | 1/1986 | McLaughlin et al. | ........ 502/410 |
| 4,746,517 A | * | 5/1988 | Ducroo | ............................ 426/12 |
| 5,453,285 A | * | 9/1995 | Versteegh | ........................ 426/29 |
| 5,460,836 A | * | 10/1995 | Ono et al. | ........................ 426/11 |

(Continued)

FOREIGN PATENT DOCUMENTS

| | | |
|---|---|---|
| DE | 2443735 A1 | 8/1975 |
| DE | 19831946 A1 | 2/2000 |

(Continued)

OTHER PUBLICATIONS

"Beer Sample—Count Cells"—available on the internet at <http://web.archive.org/web/20060519050743/http://toolboxes.flexiblelearning.net.au/demosites/series4/412/test301A/TEST301-0402-Task2CountCellsBeer.htm>, May 19, 2006.*

(Continued)

*Primary Examiner* — David A Rogers

(74) *Attorney, Agent, or Firm* — Marshall, Gerstein & Borun LLP

(57) ABSTRACT

The Invention relates to a method for determining the filterability of beer, said method having the following steps: a) taking a wort or beer sample, b) filtering the sample on a plurality of filters of varying pore size, c) determining the size of the particles on the filter surfaces of the filters, d) qualitative analysis of the particles on the filter surfaces and assigning the measured particles to certain substances or groups of substances present in beer or the wort, wherein evidence on the filterability can be obtained from the size of the particles of different substances or groups of substances of individual fractions.

15 Claims, 8 Drawing Sheets

(56) References Cited

U.S. PATENT DOCUMENTS

| | | | | |
|---|---|---|---|---|
| 5,607,497 | A | * | 3/1997 | Brown ................. 73/864.71 |
| 5,648,246 | A | * | 7/1997 | Versteegh ................. 435/93 |
| 5,820,766 | A | * | 10/1998 | Gevertz et al. ............. 210/753 |
| 6,083,387 | A | * | 7/2000 | LeBlanc et al. ............ 210/199 |
| 6,874,357 | B2 | * | 4/2005 | Yakhno et al. ............ 73/64.53 |
| 7,254,212 | B2 | * | 8/2007 | Saitoh et al. ................. 378/47 |
| 7,641,794 | B2 | * | 1/2010 | Oka et al. ................. 210/259 |
| 2003/0168413 | A1 | | 9/2003 | Brett et al. |
| 2009/0269818 | A1 | * | 10/2009 | Festersen et al. ............. 435/93 |
| 2010/0112132 | A1 | * | 5/2010 | Luers et al. ................. 426/63 |
| 2010/0303955 | A1 | * | 12/2010 | Elvig ........................ 426/13 |

FOREIGN PATENT DOCUMENTS

| | | |
|---|---|---|
| DE | 10026723 A1 | 12/2001 |
| WO | WO-9936504 A1 | 7/1999 |
| WO | WO-2007054146 A1 | 5/2007 |

OTHER PUBLICATIONS

Timmermans, P., :Determination of the Filterability of Beer, Journal of the Institute of Brewing, Sep.-Oct. 1994.*
Goerth et al., "A Simple Method for Testing Beer Filterability", Journal of the Institute of Brewing, May-Jun. 1981.*
Ralf Waiblinger, "Beer Filterability", "The Brewer International", Jan. 2002.*
Kuiper et al., "Filtration of Lager Beer with Microsieves: Flux, Permeate Haze and In-line Microscope Observations", Journal oif Membrane Science, 2002.*
Nathan Starbard, "Beverage Industry Microfiltration—Chapter 9", Wiley-Blackwell, $1^{st}$ Edition, Oct. 2008.*
Martina Skantz, "Crossflow Microfiltration of Beer", Department of Chemical Engineering, Lund Institute of Technology, Mar. 2004.*
"A Guide to Scanning Microscope Observation", JEOL, Ltd, available on the internet at <http://web.archive.org/web/20060215000000*/http://www.geology.wisc.edu/~johnf/g777/JEOLguide.pdf>, Feb. 15, 2006.*
Japanese Office Action for K-187-113.

* cited by examiner

METHOD FOR DETERMINING THE FILTERABILITY OF BEER

CROSS-REFERENCE TO RELATED APPLICATION

The present application claims the benefit of priority of International Patent Application No. PCT/EP2009/008364, filed Nov. 24, 2009, which application claims priority of German Application No. 102008060446.1, filed Dec. 4, 2008. The entire text of the priority application is incorporated herein by reference in its entirety.

FIELD OF THE DISCLOSURE

The disclosure relates to a method for determining the filterability of beer.

BACKGROUND

As beer does not only have to exhibit a perfect odor, taste and foam, but brightness is also demanded, the beer must be artificially clarified, i.e. filtered. This procedure involves the advantage that not only turbidity constituents, such as protein, tannin compounds and hop resins, are retained here, but also yeasts and possibly bacteria. The filter is usually arranged on the filling path between the fermenting/storage tank and the filler. For example due to different raw material properties or different process managements, different beers have varying filterabilities, meaning that a varying proportion of ingredients per time unit and filter surface can be filtered out of the beer or wort, and consequently the service life of the corresponding filters is varying. One problem in filtration is that for example in case of kieselguhr filtration, a fast pressure increase at the filter surface might occur, resulting in a shorter filter service life.

Up to present, one has assumed that beers having similar compositions, e.g. similar proportions of beta glucan, protein contents etc., and a similar viscosity have similar filterabilities. However, internal tests revealed the following:

FIG. 3 shows, as an example, the proportion of beta glucan, total nitrogen and magnesium-precipitable nitrogen, as well as the viscosity for a standard beer and a beer that was manufactured by means of a mash vessel in which a vibration unit (or several vibration units) is provided which oscillates the mash. Such a mash vessel is illustrated, for example, in DE 10026723 A1. Although the beers manufactured with and without vibration unit(s) have essentially the same compositions, as is shown in FIG. 3, these nevertheless have different filterabilities, as can be clearly seen in FIG. 5.

In FIG. 5, one can see the increase in the pressure difference in a kieselguhr candle filter. The left half shows the pressure increase of the beer 1 ($\alpha$1), the right half shows a classically brewed beer ($\alpha$2). One can clearly see that the pressure increase in the left half has a flatter progress ($\alpha$1<$\alpha$2). Thus, in beer 1, a higher amount of beer can be filtered until the maximum admissible pressure difference at the filter is reached. However, this means that with the former analysis techniques, i.e. for example the determination of the beta glucan proportion, the viscosity, etc., no reliable statement on filterability can be made.

SUMMARY OF THE DISCLOSURE

Therefore, it is one aspect of the present disclosure to provide a method for determining the filterability of beer.

So, according to the present disclosure, in a step a), a wort or beer sample is taken. To give a statement on the particle size distribution of individual substances or groups of substances, the sample is filtered in a step b) on a plurality of filters of varying pore sizes. By the sample being filtered successively on a plurality of filters, different fractions remain on the filter surfaces, so that in a step c) the size of the particles on the filter surface can be reliably and easily determined. Here, of course not the complete filter surface must be examined. It is sufficient to examine a representative section of the filter surface. Then, in a step d), by a qualitative analysis of the particles of varying sizes on the corresponding filter surfaces, the particles can then be assigned to certain substances or groups of substances present in the beer.

Advantageously, steps c) and d) are performed for all fractions. However, it is also possible to only perform these steps for some selected fractions. Step d) can also be performed before step c).

Thus, the size of the particles of different substances or groups of substances of individual fractions can be determined. This is a measure for the filterability of the beer. Thus, by means of the method according to the disclosure, a prediction on filterability can be made, i.e. on the dimension of the proportion of undesired beer ingredients that can be filtered out of the beer or wort per time unit and filter surface, and on the approximate expected service life of the filter surface. According to a preferred embodiment, the particle size distribution of a substance or a group of substances in the sample is determined. For this, the number of particles of a certain size of a certain substance or a group of substances can then also be determined.

It was not known up to now that the size of different substances or groups of substances or its particle size distribution has an essential influence on filterability.

Advantageously, a laboratory or sample filter, in particular a membrane filter, is used as a filter. Laboratory filter is defined as a filter which has clearly smaller filter surfaces than a filter for beer filtration. With the aid of such a membrane filter, the method can be particularly easily performed as the sample only has to be conducted through a certain membrane and this can then be easily removed.

It is a great advantage if the technologist can make a prediction on filterability as he can then adjust parameters of the beer manufacturing process and/or the filtering process depending on the size of the particles of different groups of substances of individual fractions.

It is particularly advantageous if in step c) the size of the particles is determined by means of a scanning electron microscope (SEM). The size of the particles can be easily measured in this way. Size of the particles is defined in particular as their maximum lengths, areas or diameters.

It is particularly advantageous if the qualitative analysis of the particles in step d) is performed by means of an EDX method (energy-dispersive X-ray analysis). For this, microrange analytics in the micro and/or nanometer range can be performed, and the image generated by the scanning electron microscope can be used for identifying the particles. Thus, the composition of the residues on the filter surfaces, i.e. the particles, can be determined in a simple manner. As the major portion of the substances or groups of substances, respectively, in the beer is organic, i.e. is based on carbon, the distinction of the particles can be made with reference to certain indicators (e.g. nitrogen for proteins). With this method, the surface topography can be very well represented.

Advantageously, two to six filters, but in particular three to five filters, each with different pore widths, are successively used. The pore widths are here within a range of 0.1 to 20 µm, preferably 0.45 to 10 µm. Thus, the particles of varying sizes can remain on the filter surfaces and be easily measured.

The groups of substances comprise, for example, beta glucan, beta glucan gels, polyphenols (tanning agents), higher dextrins, proteinaceous substances. The present disclosure will be illustrated below in greater detail with reference to the following figures.

Advantageously, the filter layer is coated before the EDX analysis, in particular with a metal layer or a carbon layer. Thus, the particles can be fixed on the filter surface for the analysis. Thereby, the image quality can be improved.

It is advantageous to dilute the sample before filtration. Thus, the formation of a cover layer on the filter surfaces can be prevented, and the individual particles can be reliably examined.

The qualitative analysis in step d) can also be effected optically by comparing the appearance of the particles.

BRIEF DESCRIPTION OF THE DRAWINGS

The present disclosure will be illustrated below in greater detail with reference to the following figures.

DETAILED DESCRIPTION OF THE PREFERRED EMBODIMENT

Hereinafter, a possible embodiment of the present disclosure for determining the filterability of beer will be illustrated more in detail.

Figure 2:
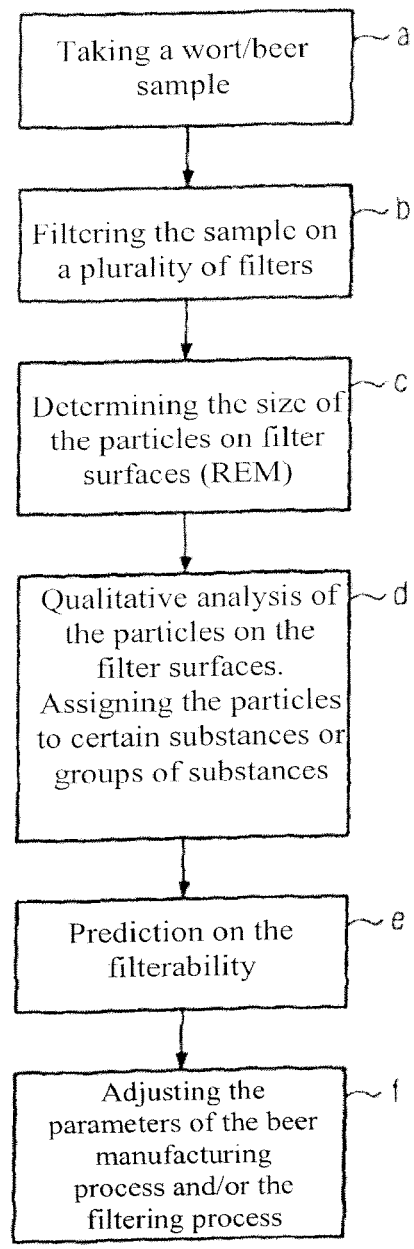
FIG. 2 shows a flow chart of an embodiment of the present disclosure.
Figure 3:
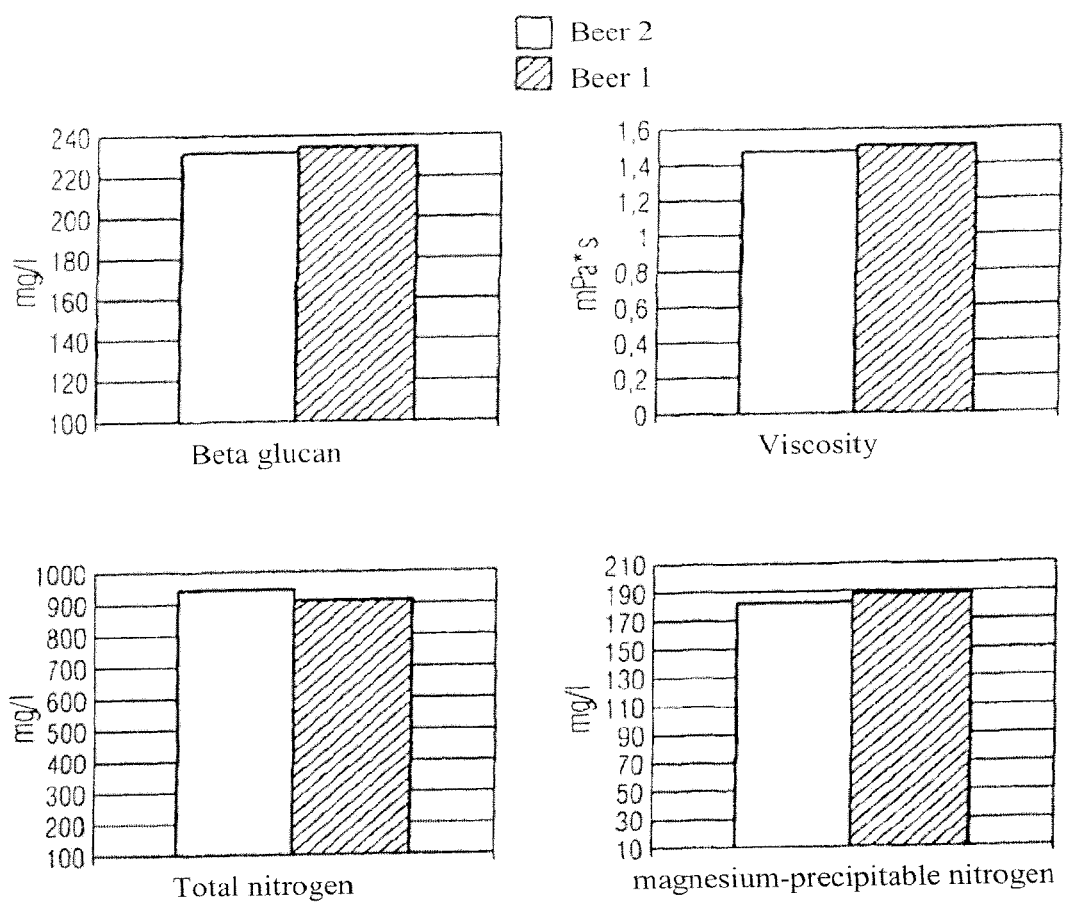
FIG. 3 shows properties of two different beers.

As can be taken in particular from the flow chart in FIG. 2, first a wort or beer sample of the beer to be filtered is taken from the production (a). The beer sample here comprises, for example, a volume of 100 to 200 ml. In the laboratory, a suited dilution of e.g. 1:4 to 1:10, e.g. with water, is then preferably prepared. A dilution is advantageous because then a particle cover layer on the respective filter surfaces can be prevented, so that the individual particles on the filter surface can be examined.

Figure 7:
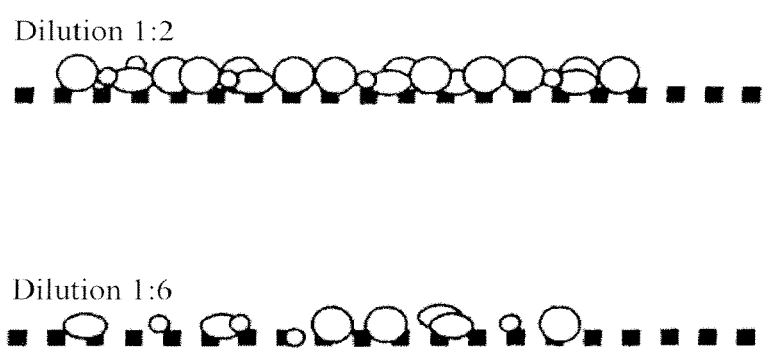
FIG. 7 shows the particle density on the filter surface in different dilutions.

FIG. 7 shows, by way of example, the particle density on a filter surface with a dilution of 1:2. Here, the particle density is so high that an examination of the individual particles is hardly possible. With a dilution of 1:6, the particle density is lower, so that a quantitative (counting the particles, determining the size) as well as a qualitative analysis is easily possible.

As a starting volume for the method, then for example a diluted sample with a volume of 100 ml is provided. This sample is then filtered successively over a plurality of laboratory filters, here membrane filters of varying pore sizes (b).

Figure 6:
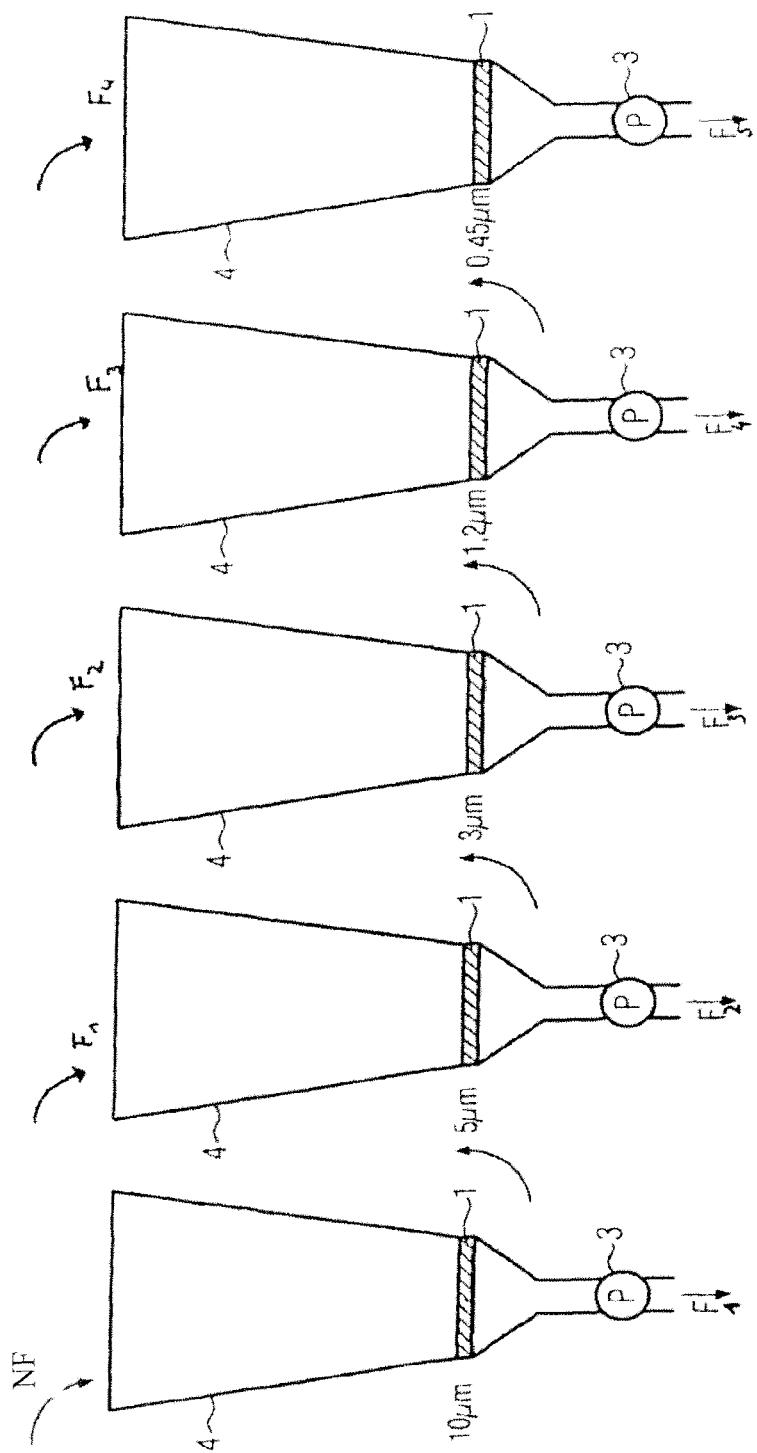
FIG. 6 shows an arrangement of a plurality of filters according to the present disclosure.

Successively means, as can be seen in FIG. 6, that the filtrate F of a first filter is supplied to the subsequent filter as nonfiltrate NF until the sample has passed all filters. The pore width of the different filters is within a range of 0.1 to 20 µm, preferably 0.45 to 10 µm. In this concrete embodiment, for example membrane filters with membranes of a pore size of 10 µm, 5 µm, 3 µm, 1.2 µm and 0.45 µm are employed, as can be in particular taken from FIG. 6. The filters having a large pore width, in particular the first and the second filters, serve to separate the yeasts. Fractioning should be performed with at least two to six, preferably with at least three to five membrane filters.

By fractioning, the particles in the sample, in particular the diluted sample, can be divided into different size ranges.

Figure 8:
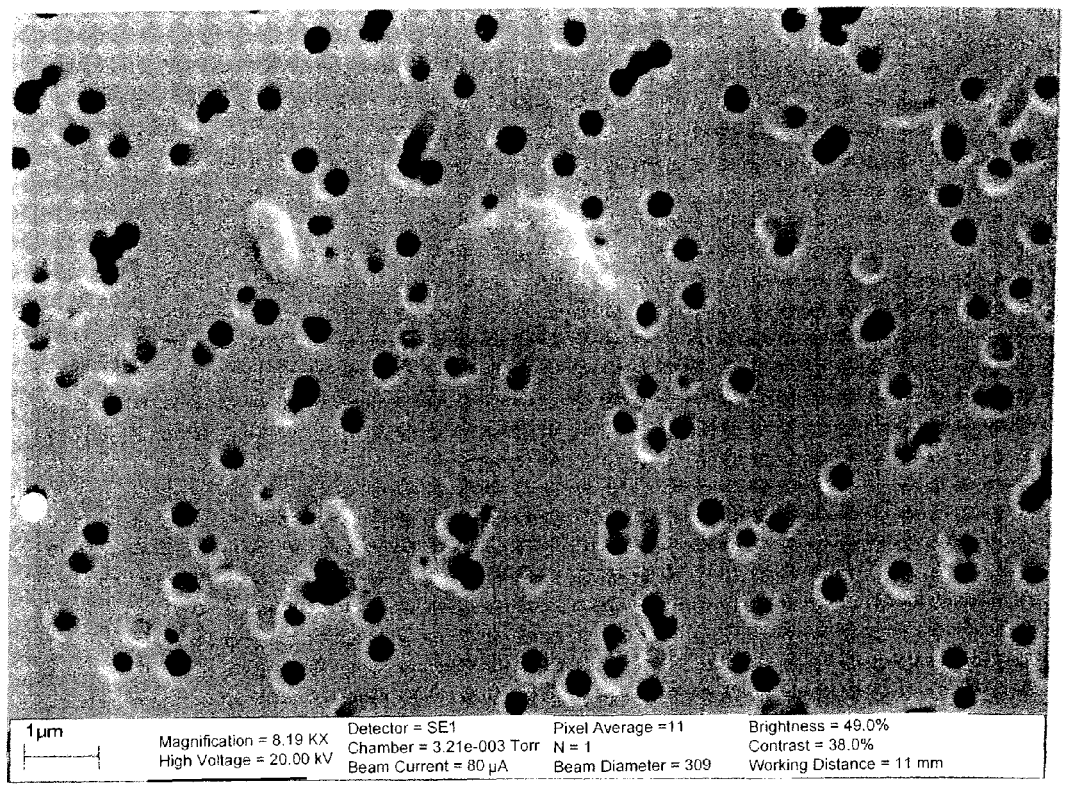
FIG. 8 shows the surface of an enlarged plane filter surface which is particularly suited for the present disclosure.

The filter surface 1, i.e. the membrane, is arranged in the filter such that it can be replaced. The nonfiltrate can, as is shown in FIG. 6, filled into a nonfiltrate space 4, here a hopper, and by means of a pump P (e.g. a water jet pump) drawn through the filter membrane. Thus, particles of varying sizes remain on the individual filter surfaces, i.e. on the individual membranes. The size of the filter surface 1 is, for example 10-30 $cm^2$. As a filter, a filter with a plane surface is particularly suited, meaning that the surface is not shrubby or rugged. Such a filter surface is shown in FIG. 8 in an 8.19K X enlargement. This has the advantage that the filtered particles are all more or less lying on one plane. This is advantageous for the subsequent qualitative examination. A polycarbonate filter, in particular a nitrogen-free filter with a honeycomb structure, proved to be very suited.

In a next step (c), the size of the particles on the filter surface shall now be determined. Here, either the complete filter surface, or else a representative section of the filter surface can be examined. For this, the filter surface is removed from the filter. The filter surface under examination is preferably within a range of 0.5-4 $cm^2$, e.g. a square with an edge length of 1 cm.

Figure 4A:
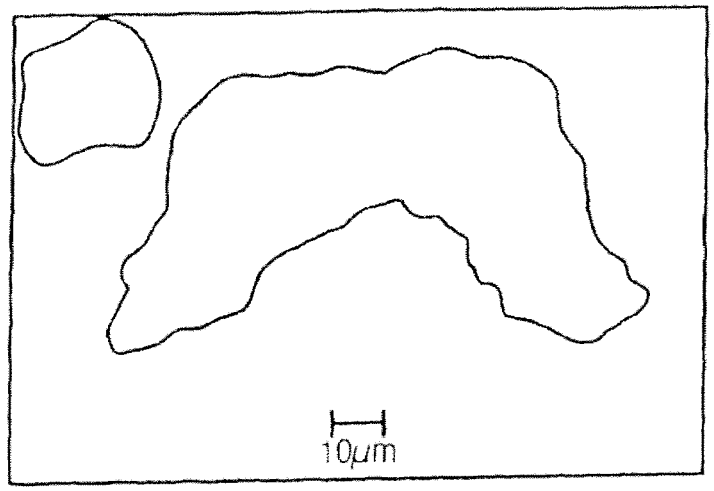
FIG. 4A shows a scanning electron microscope image of a filter surface section.
Figure 4B:
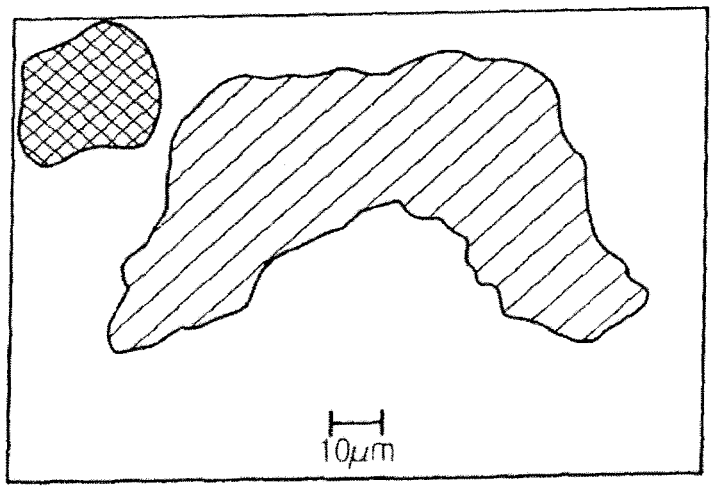
FIG. 4B shows a qualitative analysis of the element composition of the image shown in FIG. 4A.
Figure 5:
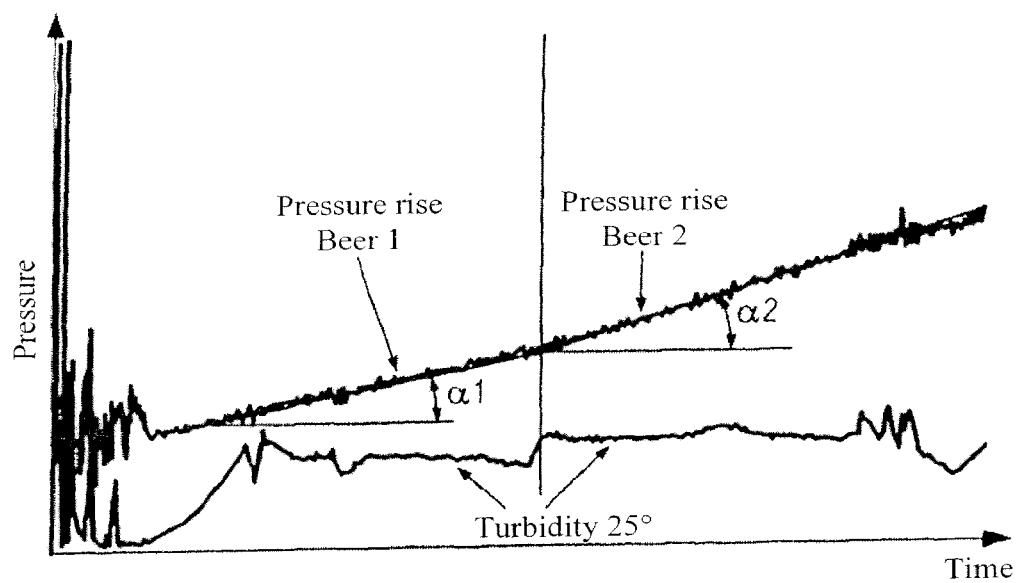
FIG. 5 shows the different pressure increase in the filtration of two different beers.

It is particularly advantageous if the size of the particles is measured by means of a scanning electron microscope. Size of the particles is defined as their maximum lengths, areas or diameters. FIG. 4A, for example, shows a section of a scanning electron microscope which shows two particles on the filter surface.

Finally, a qualitative analysis of the particles (c) on the filter surfaces is performed. Advantageously, this qualitative analysis is performed by means of an EDX method (energy-dispersive X-ray analysis). For the qualitative EDX analysis, it is advantageous for the filter surface to be thinly coated with the particles, i.e. e.g. a metal coating (e.g. gold, platinum), or a carbon coating is deposited on it, in particular by sputtering. This helps to fix the particles, as otherwise the electron beam could blast away the particles. By the coating over the filter surface, the image quality is moreover improved. If the coating is applied before the particle size is measured, the layer thickness can be taken into consideration in measuring and subtracted.

In the EDX method, an electron beam strikes the sample surface. By interaction between electrons and the sample, X-rays are released. The X-rays are detected, where element-specific bands for the element analysis are used. As the major portion of the beer is organic, i.e. is based on carbon, the distinction of the particles can be made with reference to indicators (e.g. nitrogen for proteins). For the other substances or groups of substances, the proportion of the elements must be evaluated. As can be taken from picture 4B, the scanning electron microscope or the surface of the sample, respectively, is then represented in different ways of representation (e.g. colors) which correspond to the corresponding detected elements. Advantageously, a combined SEM/EDX apparatus is used.

It is equally possible to change the sequence of steps c and d, so that first the qualitative analysis of the particles is performed, and then the size of the corresponding particles is determined.

In any case, the measured particles can then be assigned to the substances or groups of substances present in the wort or beer (d). Such groups of substances comprise, for example, beta glucan, beta glucan gels, polyphenols, higher dextrins, proteinaceous substances. The relatively large yeasts mainly remain on the first, coarsest filter, so that for the yeasts, no further analysis with respect to size or composition is made. The first filter therefore must be normally not subjected to any further analysis and thus only serves as a pre-filter to be able to better detect the particles of the subsequent fractions. Thus, a difference in the particle sizes of the individual substances or groups of substances in the individual fractions can be determined. Moreover, not all particles on the filter surface must be measured, but a representative quantity is sufficient.

Figure 1:
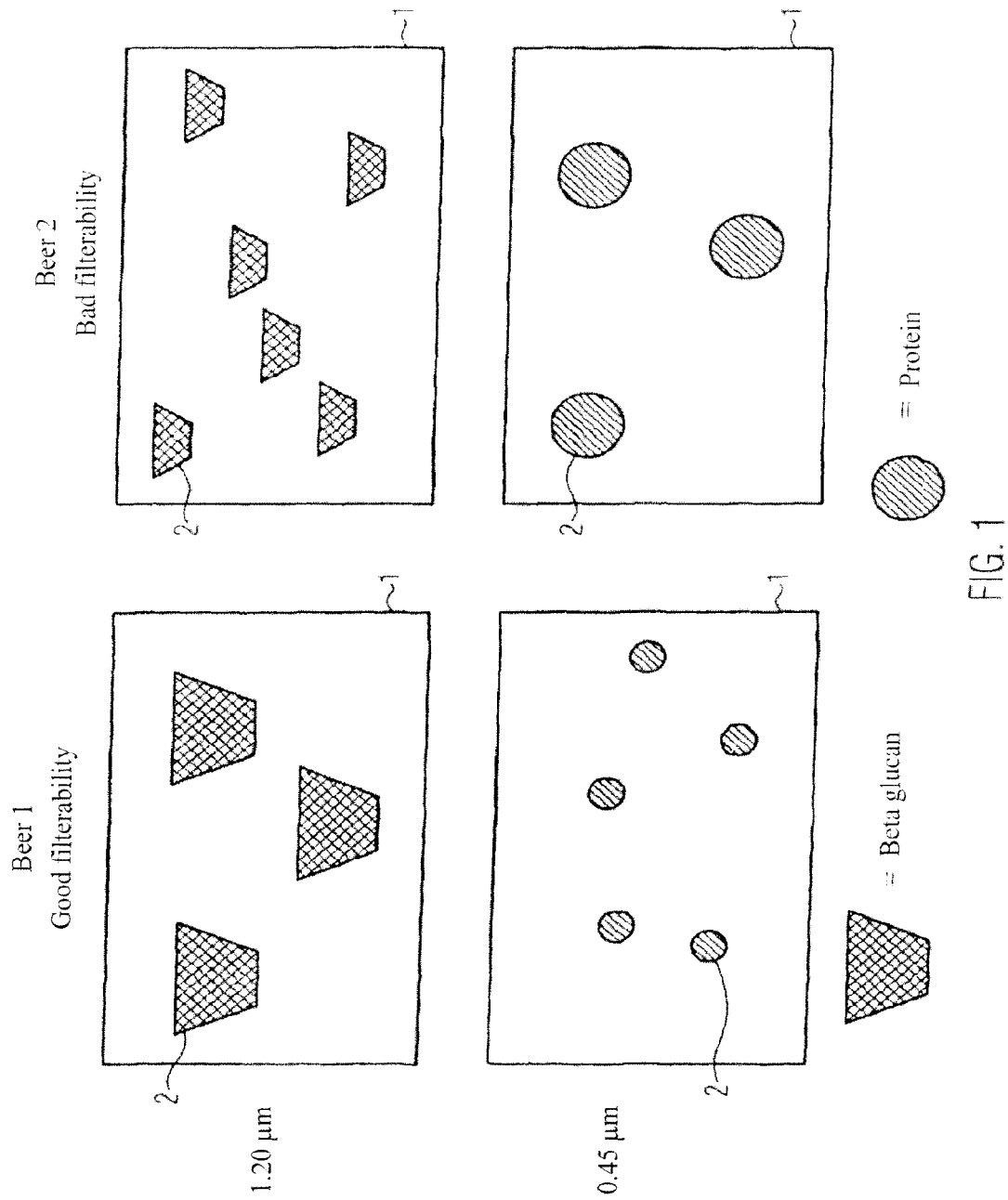
FIG. 1 shows, in a schematic representation, the filterability in response to the particle size of varying groups of substances for two different beers.

FIG. 1 shows the results of steps a to d for a beer 1, as well as the results for a beer 2. Beer 1 is a standard beer, while beer 2 was subjected to a vibration process during mashing, as was illustrated in the introduction of the description. Here, only the filter surface sections of the filters with a pore width of 1.2 µm and 0.45 µm are represented. In FIG. 1, only two fractions are represented. It is also possible to include all fractions in the assessment.

As can be taken from FIG. 1, with the pore size of 1.2 µm, the beer 1 includes large beta glucan particles. The beta glucan particles here for example have a size within a range of 5 to 10 µm. In the fraction of the filter surface with a pore size of 0.45 µm, beer 1 contains relatively small protein particles which have, for example, a size of 0.5-1.0 µm.

In contrast to this, beer 2 in the 1.2 µm fraction exhibits smaller beta glucan particles which comprise a size of 2-3 µm, for example. In contrast to this, on the filter surface of the 0.45 µm fraction, there are relatively large protein particles which have a size of 1-1.2 µm, for example.

It is also possible to form an average value of the size of particles of a certain group of substances of a certain fraction.

However, essentially all particles of a substance or a group of substances can be also counted on the filter surface or the certain section of the filter surface, so that then the particle size distribution of the substance or the group of substances in the complete sample can be determined.

The results are then compared to comparative results that have been determined in comparative tests. In the corresponding comparative tests, the filterability with different sizes of the particles of certain substances or groups of substances has been determined.

For example, beer 1 with very large beta glucan particles and small protein particles has a better filterability than beer 2 which has smaller beta glucan particles, but larger protein particles. This means that in beer 1, a larger proportion of beer ingredients per time unit and filter surface can be filtered out of the beer or the wort, and a longer service life of the filter can be expected than in beer 2. This is e.g. because the larger beta glucan particles keep the beer filter surface loose and the small protein particles can therefore better pass the filter.

This means that a prediction on the filterability can be made (e).

The technologist thus has the possibility of intervening purposefully in the beer manufacturing process and/or the filtering process depending on the determined size of the particles of different groups of substances. (f)

In precoat filtration, a correspondingly coarser or finer kieselguhr mixture in the dosage as well as an adapted cellulose proportion in precoating can then be planned. This means that for example in beer 2, which has a worse filterability, a dosage with a coarser kieselguhr proportion and a higher cellulose proportion can be prepared in precoating.

In kieselguhr filtration, i.e. filtration without any filtering aids, at least the production planning can be calculated more precisely.

A prediction on filterability should be made from a sample of the starting wort or even earlier from a sample of the congress wort. Furthermore, the beer fermented to completion, for example from the starting wort or the congress wort, can be used as a sample. Moreover, for example the beer fermented to completion from the production process of the beer manufacture can be also used as a sample. Here, the differently produced beers 1 and 2 were stated as an example. For the sake of good order, however, it should be noted that different filterabilities also result due to different raw material properties in identical manufacturing processes.

The qualitative analysis or the assignment to various substances or groups of substances can be performed by the above-described instrumental analytics and/or optically; i.e. also on the basis of the special shape or the appearance of the particles (such as, for example, porous, compact, smooth, spherical, structured, gel-like), and by comparing the special shape or appearance of the particles represented in the microscope (SEM) with the shape of certain substances or groups of substances of individual fractions previously determined under the microscope (SEM).

The completely new approach of assessing the filterability depending on the size of different substances or groups of substances finally permits an improved filtration method in which the filters have longer service lives.

The invention claimed is:

1. Method in particular for determining the filterability of beer, comprising:
    a) taking a wort or beer sample,
    b) filtering the sample on a plurality of filters of varying pore size,
    c) determining the size of the particles on the filter surfaces of the filters,
    d) qualitative analysis of the particles on the filter surfaces and assigning the measured particles to certain substances or groups of substances present in the beer or wort,
    e) predicting the filterability of the beer from the wort or beer sample based on the size of the particles determined in step c) and the qualitative analysis of step d),
    wherein the qualitative analysis of the particles in step d) is determined by an energy-dispersive X-ray (EDX) method; and
    wherein a coating is deposited on the filter surface before step d).

2. Method according to claim 1, and determining in the sample the particle size distribution of a substance or a group of substances.

3. Method according to claim 2, wherein predicting the filterability of the beer from the wort or beer sample based on the size of the particles determined in step c) and the qualitative analysis of step d) includes correlating the particle size distribution of the substance or the group of substances to a particle size distribution of a substance or a group having a known filterability.

4. Method according to claim 1, and:
f) adjusting parameters of the beer manufacturing process and/or the filtering process depending on the size of the particles of different groups of substances of individual fractions.

5. Method according to claim 1, and using one of a filter or a laboratory filter for the prediction of filterability.

6. Method according to claim 5, wherein the filter is a membrane filter.

7. Method according to claim 1, and in step c), determining the size of the particles by a scanning electron microscope (SEM).

8. Method according to claim 1, and successively using two to six filters, each with different pore widths, where the pore width is within a range of 0.1 to 20 μm.

9. Method according to claim 8, and successively using three to five filters.

10. Method according to claim 8, wherein the pore width is within a range of 0.45 to 10 μm.

11. Method according to claim 1, wherein the groups of substances comprise beta glucan, beta glucan gels, polyphenols, higher dextrins and proteinaceous substances.

12. Method according to claim 1, and diluting the sample before filtration.

13. Method according to claim 10, and in step b), successively filtering the sample on a plurality of filters of varying pore size.

14. Method according to claim 1, and effecting optically the qualitative analysis in step d) by comparing the appearance of the particles on the filter surface with the appearance of particles of certain substances or groups of substances.

15. Method according to claim 1, wherein the coating is one of a carbon coating or a metal coating.

* * * * *